United States Patent
Makl et al.

[11] Patent Number: 5,999,398
[45] Date of Patent: Dec. 7, 1999

[54] FEED-THROUGH FILTER ASSEMBLY HAVING VARISTOR AND CAPACITOR STRUCTURE

[75] Inventors: Albert S. Makl, Myrtle Beach, S.C.; Richard J. Panlener, Valencia; Randall J. Piersma, Santa Clara, both of Calif.

[73] Assignee: AVX Corporation, Myrtle Beach, S.C.

[21] Appl. No.: 09/104,093

[22] Filed: Jun. 24, 1998

[51] Int. Cl.⁶ .............................. H01G 4/35; H01C 7/10
[52] U.S. Cl. ................... 361/302; 361/309; 361/303; 338/20
[58] Field of Search .................. 361/301.1, 302, 361/303, 309, 306.3, 321.1, 322; 338/20, 21; 607/5, 9, 36

[56] References Cited

U.S. PATENT DOCUMENTS

| | | |
|---|---|---|
| 3,842,374 | 10/1974 | Schlicke .......................... 333/182 |
| 4,409,728 | 10/1983 | Ellis et al. . |
| 4,424,551 | 1/1984 | Stevenson et al. . |
| 4,646,037 | 2/1987 | Turolla et al. . |
| 4,675,644 | 6/1987 | Ott et al. . |
| 4,841,259 | 6/1989 | Mayer . |
| 4,887,180 | 12/1989 | Climent et al. . |
| 5,034,709 | 7/1991 | Azumi et al. . |
| 5,159,748 | 11/1992 | Doone et al. . |
| 5,235,310 | 8/1993 | Cowman et al. . |
| 5,266,079 | 11/1993 | Iga ........................................ 29/25.03 |
| 5,369,390 | 11/1994 | Lin et al. . |
| 5,735,884 | 4/1998 | Thompson et al. . |
| 5,751,539 | 5/1998 | Stevenson et al. . |
| 5,870,273 | 2/1999 | Sogabe et al. ...................... 361/306.3 |

FOREIGN PATENT DOCUMENTS

0623363A2  9/1994  European Pat. Off. .

OTHER PUBLICATIONS

"EMI Filtering in Medical Implantables" by Steve Makl, *Medical Device & Diagnostic Industry*, dated Sep., 1994.

Brochure entitled "TransGuard —Multi–Layer–Ceramic Transient Voltage Suppressors," by AVX Corporation, Aug. 1994.

*Primary Examiner*—Dean A. Reichard
*Assistant Examiner*—Anthony Dinkins
*Attorney, Agent, or Firm*—Dority & Manning, P.A.

[57] ABSTRACT

A feed-through filter assembly such as may be used in an implantable medical device. The assembly includes a conductive mounting element which may be hermetically sealed to an outer housing of the implantable medical device. In many embodiments, the conductive mounting element will be a conductive canister in which a feed-through filter structure is located. Alternatively, the conductive mounting element may include a suitable subplate structure. Because the filter structure exhibits both varistor and capacitive characteristics, effective transient suppression and interference filtering is achieved in a single package. Secondary filtering may be provided downstream of the filter assembly for additional interference filtering at lower frequencies.

30 Claims, 7 Drawing Sheets

FEED-THROUGH FILTER ASSEMBLY HAVING VARISTOR AND CAPACITOR STRUCTURE

BACKGROUND OF THE INVENTION

The present invention relates generally to feed-through filters utilized to separate unwanted interference from a signal path. More particularly, the invention relates to feed-through filters utilized in implantable medical devices, such as heart pacemakers and the like.

Heart pacemakers and other implantable medical devices are constructed having an outer housing in which the necessary electronic components are contained. The outer housing must be formed of a material which is compatible to be placed inside the human body. It is also important to shield the electronics within the housing from external sources of electromagnetic interference (EMI). Titanium is often utilized to satisfy these dual requirements of shielding and biocompatability.

At least one elongate lead will generally extend from the electronics within the outer housing to a desired location inside the body. While the outer housing may shield the internal electronics from direct EMI radiation, steps are also taken to inhibit transmission of EMI along the lead itself. For example, selected capacitive and/or inductive components may be mounted on a circuit board along with the other internal electronics to provide EMI filtering. Alternatively, a feed-through filter may be provided at the location where the elongate lead passes through the outer housing. Such a feed-through filter is shown and described in U.S. Pat. No. 4,424,551, incorporated herein by reference.

Although pacemaker signals are relatively low voltage, capacitors utilized in feed-through filtering arrangements must often be constructed to withstand relatively high voltage levels. This is to ensure that the capacitor does not become damaged if subjected to voltage transients, such as those caused by undesirable defibrillation pulses or the like. Generally, however, a capacitor having a higher voltage rating will be larger than a lower voltage capacitor of the same capacitance value. In view of the general trend toward miniaturization in electronic devices, larger components are often considered to be undesirable.

SUMMARY OF THE INVENTION

The present invention recognizes various disadvantages of prior art constructions and methods. Accordingly, it is an object of the present invention to provide a novel feed-through filter assembly.

It is another object of the present invention to provide a novel feed-through filter assembly exhibiting both EMI filtering and transient suppression characteristics.

It is a further object of the present invention to provide a novel filtering arrangement for use in an implantable medical device which also exhibits effective transient suppression.

Some objects of the present invention are achieved by a feed-through filter comprising a conductive mounting element. At least one elongate terminal member is maintained in electrically insulated relation with respect to the conductive mounting element. A varistor structure, defining a respective feedthrough hole through which the elongate terminal member extends, is supported by the conductive mounting element. The varistor structure has a plurality of first polarity plates interleaved with a plurality of second polarity plates. The first polarity plates are electrically connected to the elongate terminal member. Likewise, the second polarity plates are electrically connected to the conductive mounting element.

Other objects of the present invention are achieved by a feed-through filter comprising a conductive canister. At least one elongate terminal member is maintained in electrically insulated and hermetically sealed relation with respect to the conductive canister. A discoidal varistor structure, defining a respective feedthrough hole through which the elongate terminal member extends, is supported by the conductive mounting element. The varistor structure has at least one first polarity plate situated in respective opposition to at least one second polarity plate. The first polarity plate is electrically connected to the elongate terminal member. Likewise, the second polarity plate is electrically connected to the conductive canister.

Still further objects of the present invention are achieved by a filtering arrangement for use in an implantable medical device. The arrangement comprises a conductive mounting element adapted to be connected to an outer shell of the implantable medical device in hermetically sealed relation therewith. At least one elongate terminal member is maintained in electrically insulated and hermetically sealed relation with respect to the conductive mounting element. A first filter structure, operative to filter interference signals carried by the elongate terminal member above a predetermined threshold frequency as well as to provide voltage transient suppression, is supported by the conductive mounting element. A first polarity terminal of the first filter structure is electrically connected to the elongate terminal member. A second polarity terminal of the first filter structure is electrically connected to the conductive mounting element.

The filtering arrangement further comprises a second filter structure having a first polarity terminal electrically connected to the elongate terminal member. The second filter structure is operative to filter interference signals carried by the elongate terminal member below the predetermined threshold frequency. Often, the second filter structure may comprise a multilayer capacitor structure having a capacitor feedthrough hole through which the elongate terminal member extends. In some such cases, the multilayer capacitor structure may be mounted axially adjacent to the first filter structure. Alternatively, the multilayer capacitor structure may be mounted axially separated from the first filter structure. In other embodiments, the second filter structure may comprise a surface mount capacitor.

Additional objects of the present invention are achieved by a feed-through filter comprising a conductive mounting plate. A plurality of elongate terminal members are maintained in electrically insulated relation with respect to the conductive mounting plate. A varistor array structure, defining a plurality of feedthrough holes through which the elongate terminal members respectively extend, is supported by the conductive mounting plate. The varistor array structure includes a plurality of varistor devices associated with a respective one of the elongate terminal members. Each of the varistor devices has at least one first polarity plate electrically connected to the associated elongate terminal member. At least one second polarity plate is also provided, electrically connected to the conductive mounting plate.

Other objects, features and aspects of the present invention are provided by various combinations and subcombinations of the disclosed elements, as well as methods of practicing same, which are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings, in which.

Figure 1:
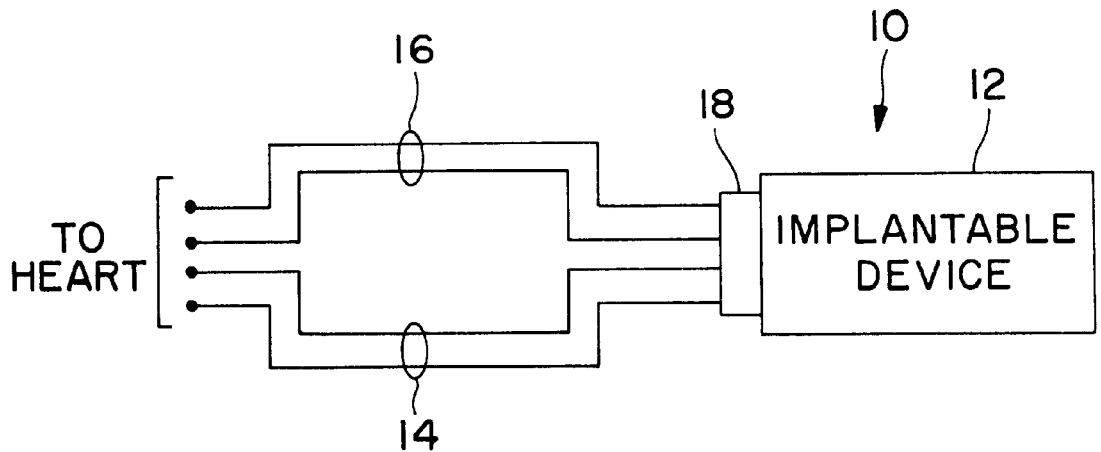
FIG. 1 is a diagrammatic representation of an implantable medical device and associated leads.

Repeat use of reference characters in the present specification and drawings is intended to represent same or analogous features or elements of the invention.

DETAILED DESCRIPTION OF PREFERRED EMBODIMENTS

It is to be understood by one of skill in the art that the present discussion is a description of exemplary embodiments only, and is not intended as limiting the broader aspects of the present invention, which broader aspects are embodied in the exemplary constructions.

FIG. 1 illustrates an implantable medical device 10 with which filtering arrangements of the present invention can be advantageously utilized. In the case of a heart pacemaker, device 10 will typically include circuitry to monitor and maintain a desired pulse rate. In some current designs, the device may also include defibrillation circuitry within the same enclosure. The various electronic components are typically contained in an outer housing 12 suitably formed to provide both biocompatability and EMI shielding. Toward this end, housing 12 is often configured as a titanium shell.

As can be seen, several leads extend from within housing 12 to selected locations inside the human body. In this case, two of the leads (collectively indicated at 14) are dedicated to heart pacing functions. The remaining two leads (collectively indicated at 16) provide defibrillation when required. A feed-through filter assembly 18 is positioned on housing 12 to separate unwanted interference picked up by the leads before it is passed to the internal electronics.

Figure 2:
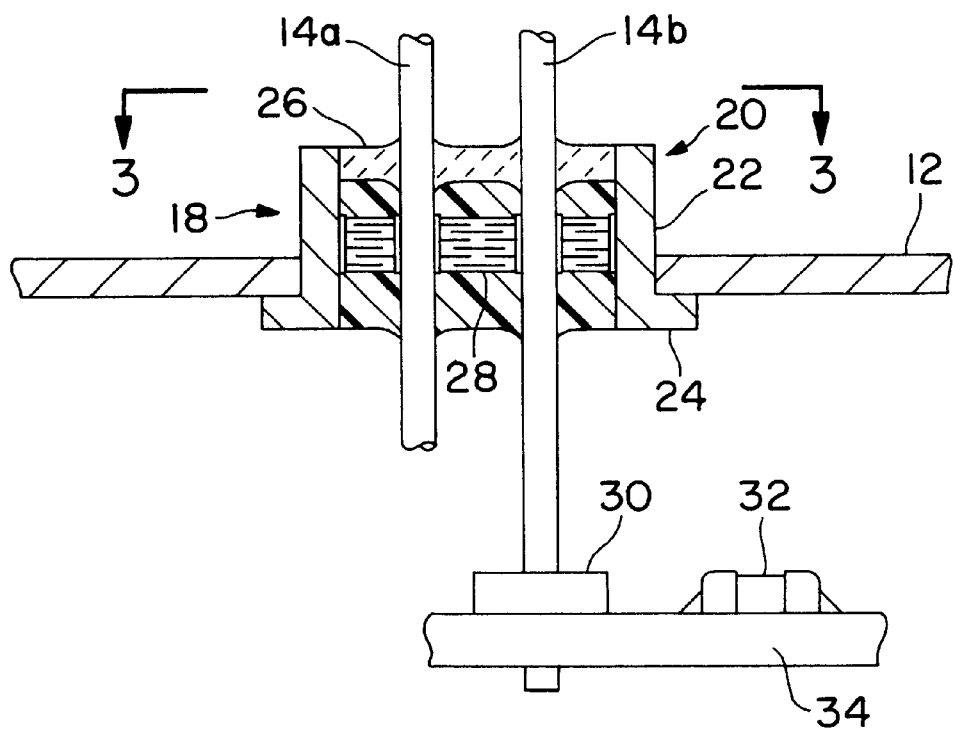
FIG. 2 is a cross-sectional view of a feed-through filter assembly of the present invention as installed in an implantable medical device, further showing secondary filtering structures that may also be utilized.

Referring now to FIG. 2, filter assembly 18 includes a conductive canister 20 having a main canister portion 22 and a weld flange 24. In an implantable medical device, canister 20 will be hermetically sealed to outer shell 12, typically by welding about flange 24. As shown, the various leads extend through canister 20 to the interior of housing 12. To prevent a short circuit, the leads, such as leads 14a and 14b, are electrically insulated from canister 22. A disc 26 of nonconductive material such as glass or the like hermetically seals the leads in the desired nonconductive relation.

As shown, a filter structure 28 is potted within the main canister portion 22 of conductive canister 20. The leads pass through respective holes defined in filter structure 28, and are electrically connected to a first polarity terminal of filter structure 28 along the inside surface of each hole. An opposite polarity terminal of filter structure 28 is electrically connected to conductive canister 20, and hence shell 12, along the inside surface of main canister portion 22.

Preferably, filter structure 28 is configured as a multilayer varistor device having a plurality of first polarity plates interleaved with a plurality of second polarity plates. For example, a varistor made of a metal-oxide based ceramic may be utilized for this purpose. A material such as that used in multilayer ZnO varistors, such as the Transguard® voltage suppressors available from AVX Corporation of Myrtle Beach, S.C., is believed to be especially suitable.

Desirably, filter structure 28 will exhibit both capacitive and transient suppression characteristics. Thus, feed-through filter assembly 18 will provide protection from high voltage pulses, while simultaneously filtering undesirable EMI above a predetermined threshold frequency. In many embodiments, EMI occurring at frequencies of approximately 100 MHZ and above can be effectively eliminated at filter assembly 18.

Often, it will be desirable to provide secondary filtering for the elimination of EMI occurring at frequencies below the predetermined threshold. As will be shown below with reference to FIG. 5, this secondary filtering may be accomplished by an additional electronic component located inside of the conductive canister. Alternatively, secondary filtering components may be located within outer housing 12 of the implantable device. For example, one or more of the elongate leads may have a respective discoidal capacitor 30 situated thereabout. One or more surface mount capacitors 32 may be utilized in addition to, or in lieu of, discoidal capacitor 30. As will be appreciated, these secondary filtering components may be conventionally mounted on a circuit board 34.

Figure 2A:
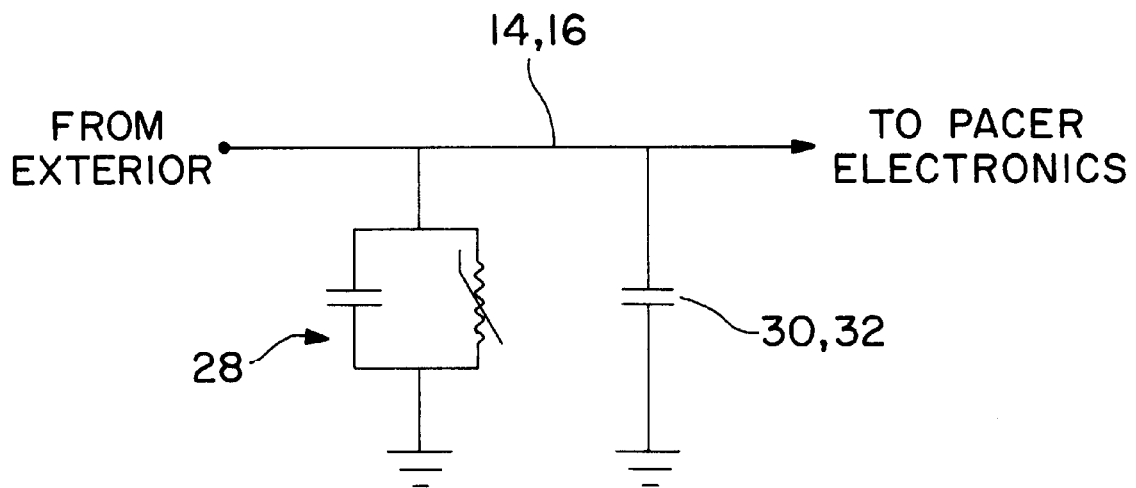
FIG. 2A is a schematic diagram of the circuit arrangement illustrated in FIG. 2.
Figure 3:
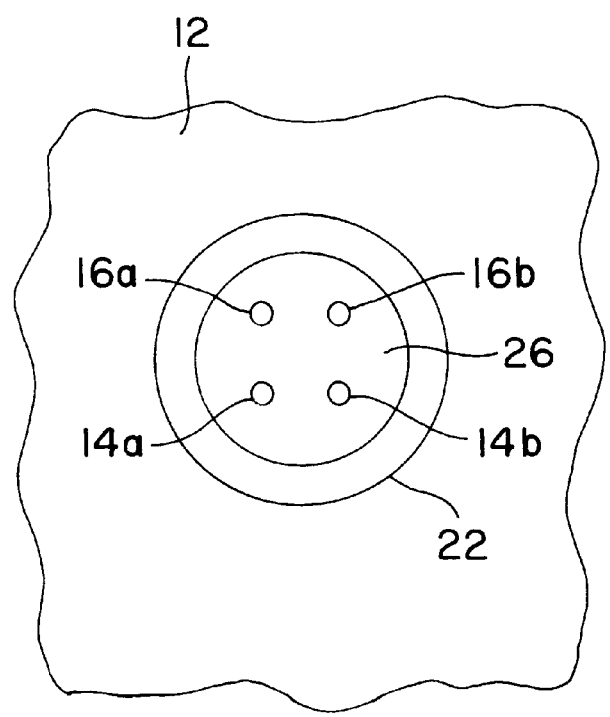
FIG. 3 is a plan view taken along line 3—3 of FIG. 2.

FIG. 2A shows the equivalent circuit realized along each elongate lead by the filtering arrangement of FIG. 2. In this arrangement, spurious signals picked up by the lead will be effectively shunted to ground before reaching the internal electronics of the implantable device. Specifically, undesirable high voltage pulses, as well as EMI above the predetermined threshold frequency, are shunted at filter assembly 28. Interference at lower frequencies may pass by filter assembly 28, but will be removed at the secondary filter (such as capacitor 30 and/or capacitor 32).

Figure 4:
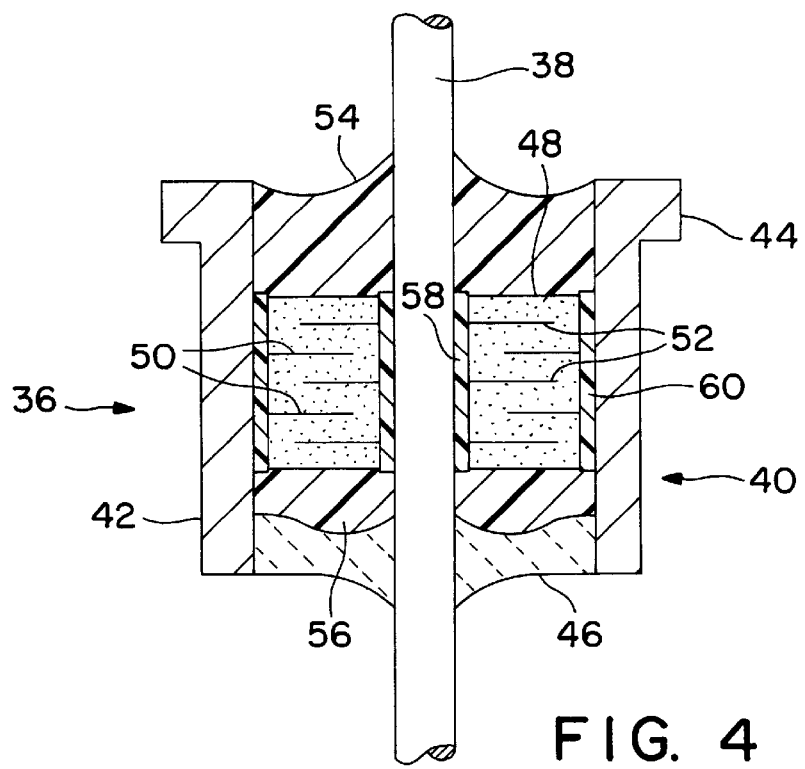
FIG. 4 is an enlarged cross-sectional view of a feed-through filter device of the present invention having a single elongate terminal member.

FIG. 4 illustrates an alternative feed-through filter assembly 36 having a single terminal member 38. The various elements of filter assembly 38 are retained and supported by a conductive canister 40. Like canister 20, conductive canister 40 has a main canister portion 42 and a weld flange 44. A nonconductive disc 46 maintains terminal member 38 in electrically insulated and hermetically sealed relation with respect to conductive canister 40.

A discoidal filter structure 48 is located inside of main canister portion 42. Preferably, filter structure 28 will be a multilayer varistor structure having a plurality of first polarity plates 50 and a plurality of second polarity plates 52. The terminals of filter structure 48 are electrically connected to terminal member 38 and conductive canister 20, respectively. In this case, filter structure 48 is potted between layers 54 and 56 of a suitable polymeric material, such as a nonconductive epoxy. As indicated at 58 and 60, a conductive epoxy may be applied at the respective terminals of filter structure 48 to complete the desired electrical connections.

Figure 5:
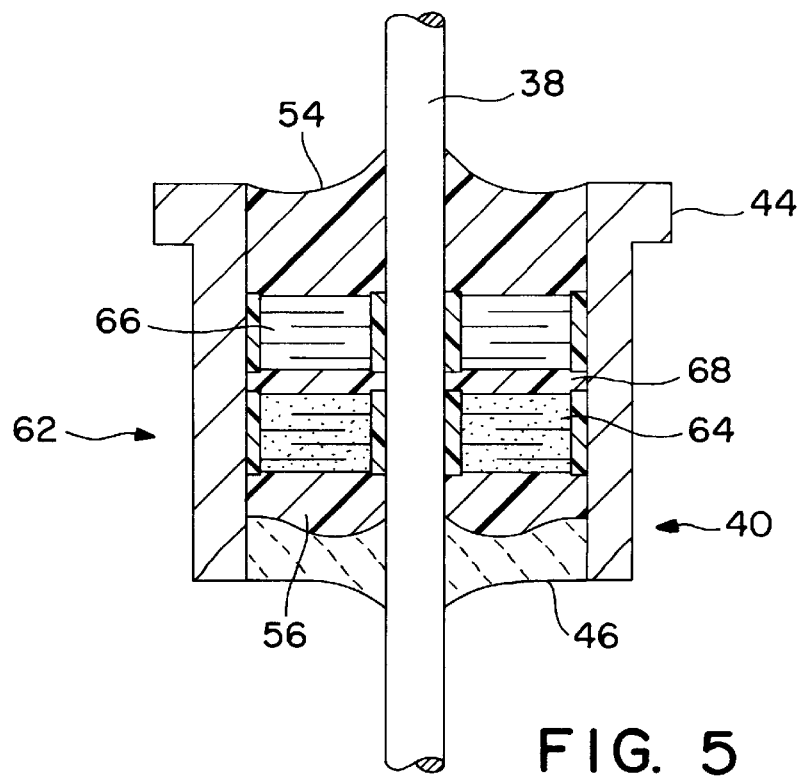
FIG. 5 is an enlarged cross-sectional view similar to FIG. 4 but showing first and second filter structures maintained within a single conductive canister.

FIG. 5 shows an alternative filter assembly 62 having many common elements with the embodiment shown in FIG. 4. In this case, however, both primary and secondary filtering structures are included in one package. Specifically, canister 40 contains both a discoidal varistor 64 and a discoidal multilayer capacitor 66. As shown, a layer 68 of epoxy may be located between the two filtering structures.

It will be appreciated that varistor 64 provides both capacitive and transient suppression characteristics. Capacitor 66, on the other hand, is intended to provide only substantially linear characteristics. Thus, varistor 64 is preferably located "upstream" to shunt incoming voltage transients before reaching capacitor 66. As a result of this construction, capacitor 66 may desirably filter EMI at lower frequencies while advantageously having a relatively low voltage rating and small size.

Conductive canisters have been described above for supporting elements of the filter assembly. It should be appreciated, however, that various subplate arrangements may also be used for this purpose. Depending on the requirements of a particular application, the filter structure may be surface mounted to the subplate, or contained within a wall integrally formed about the periphery of the subplate.

Figure 6:
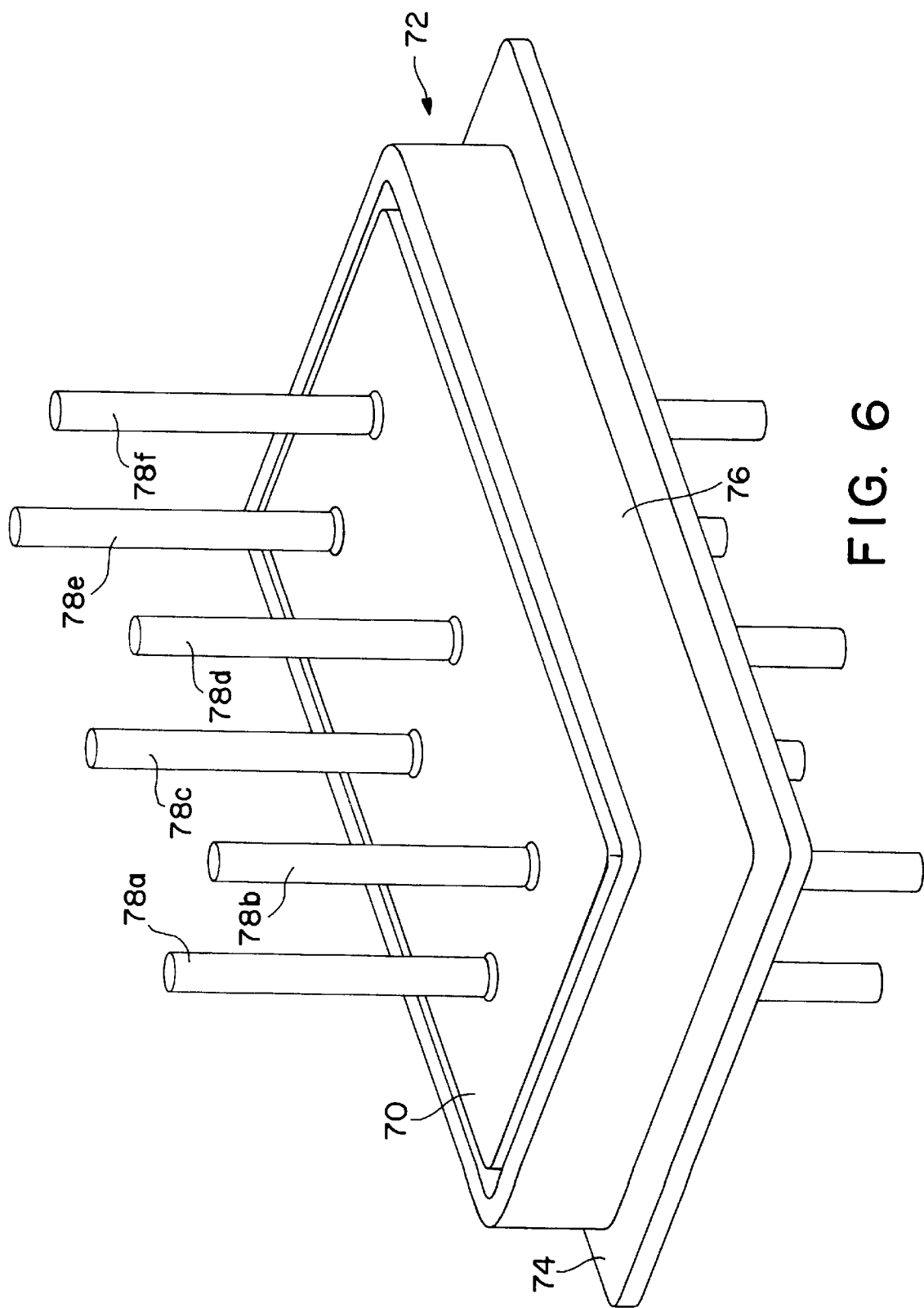
FIG. 6 is a perspective view of an alternative embodiment having a varistor array mounted to a header plate.

FIG. 6 illustrates one such embodiment, where a varistor array device 70 is mounted to a conductive header 72. Header 72 includes a bottom plate extending into a weld flange 74. A peripheral wall 76 extends up from the bottom plate to surround the varistor array 70, as shown. A plurality of terminal leads 78a–f, supported in insulated relation with the bottom plate, extend through respective holes defined in varistor array 70. Individual glass discs may be used to support the respective terminal leads in the bottom plate, while desirably providing a hermetic seal.

The manner in which multiple varistor devices are provided by varistor array 70 can be most easily explained with reference to FIGS. 6A and 6B. Preferably, array 70 is constructed as a multilayer composite structure, having multiple opposite polarity electrodes interleaved to form a stack. It should be appreciated, however, that single layer varistor structures are within the scope of the present invention where appropriate.

Figure 6A:
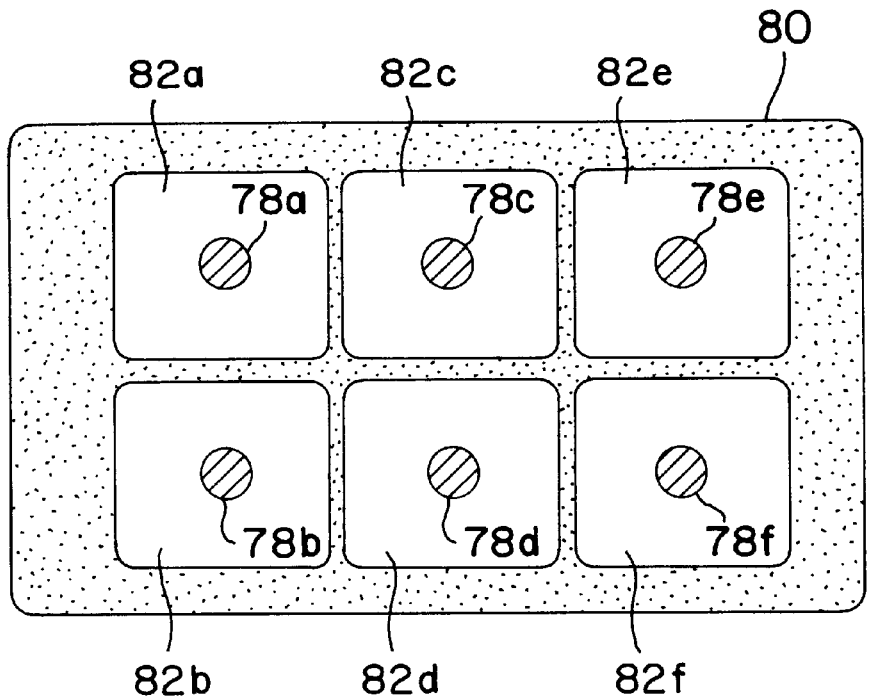
FIG. 6A is a plan view of a single layer of the varistor array of FIG. 6 showing first polarity plates associated with each of the terminal leads.

FIG. 6A illustrates a first polarity layer that may be employed in a multilayer composite structure. This layer comprises a ceramic varistor substrate 80 having a plurality of identical electrode plates 82a–f defined thereon. As can be seen, electrode plates 82a–f are electrically connected to respective terminal leads 78a–f.

Figure 6B:
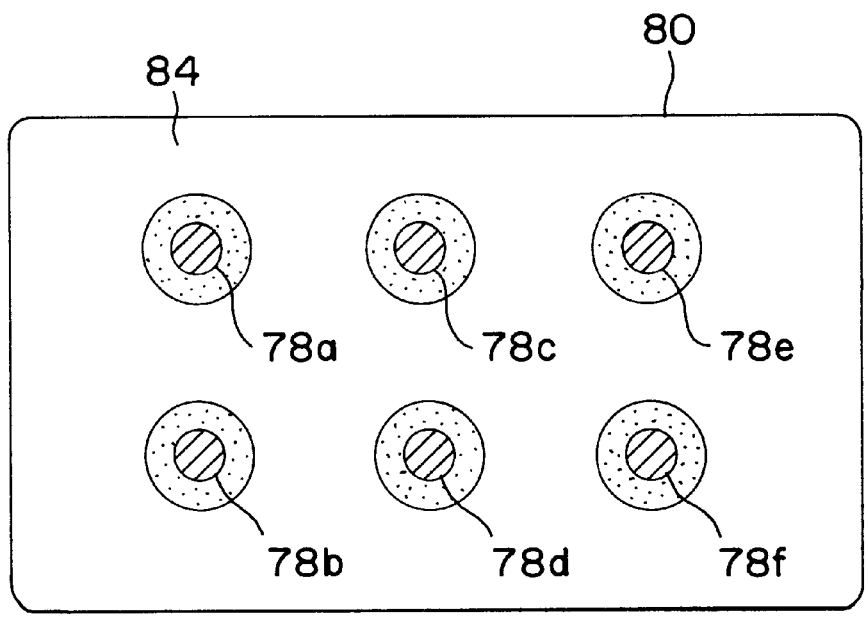
FIG. 6B is a plan view of a single layer of the varistor array of FIG. 6 showing a common second polarity plate.

A second polarity layer of the composite multilayer structure is illustrated in FIG. 6B. In this case, ceramic substrate 80 includes a single electrode plate 84 covering much of its surface. Plate 84 extends to the edge of substrate 80, permitting electrical connection with header 72 at the outer surface of array 70. Gaps are defined in electrode plate 84 about each of the terminal leads to prevent electrical connection therebetween.

Figure 7:
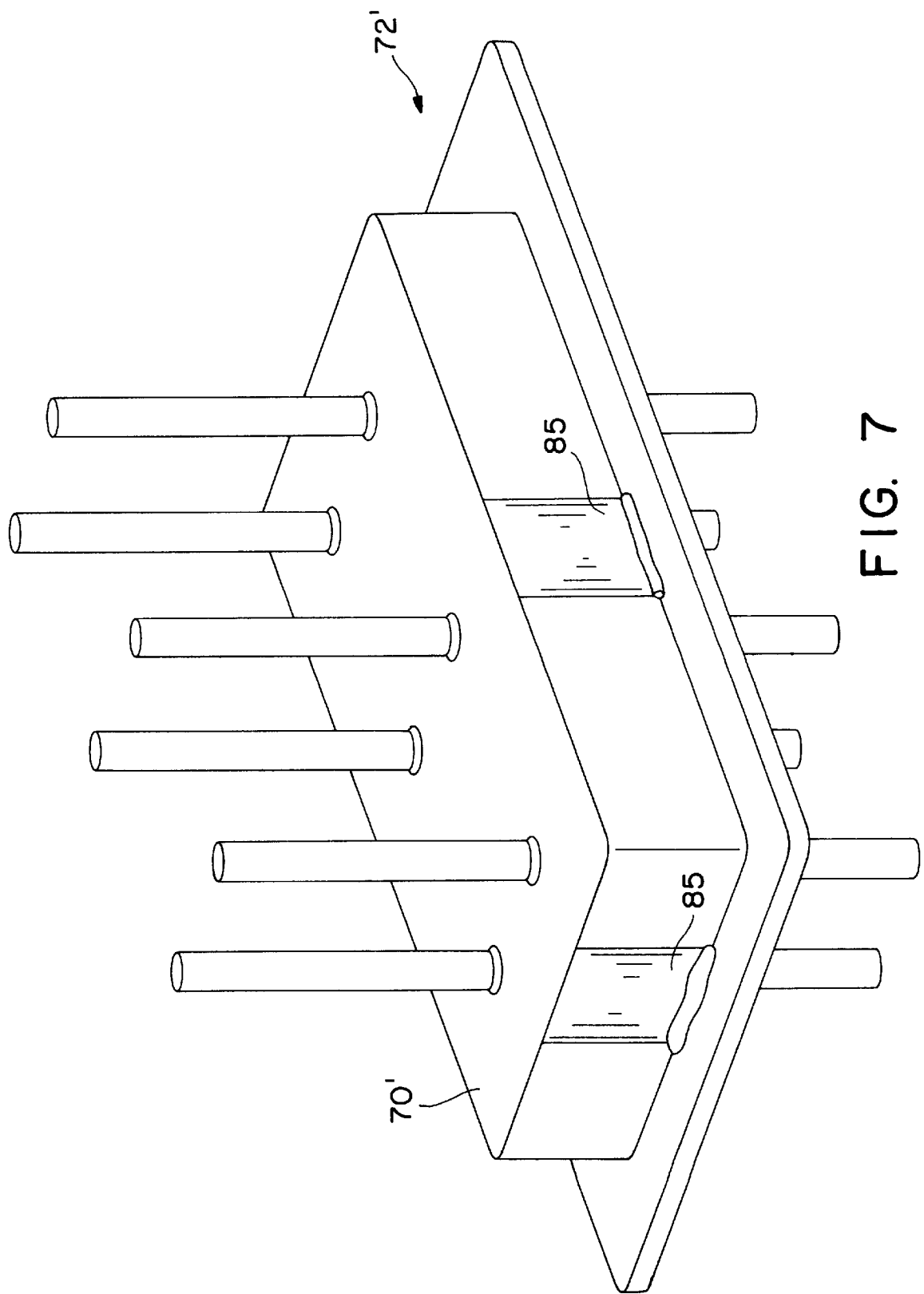
FIG. 7 is a perspective view similar to FIG. 6 illustrating a capacitor array mounted to a conductive header without a peripheral wall.

FIG. 7 illustrates a further embodiment similar to that shown in FIG. 6. In this case, however, varistor array 70' is surface mounted to a generally planar header 72'. The side surfaces of array 70' each include a "grounding tab" 85, i.e., metallized pickups, of the polarity opposite to the leads. Tabs 85 may be attached to the header plate by conductive epoxy or other suitable means.

Figure 8:
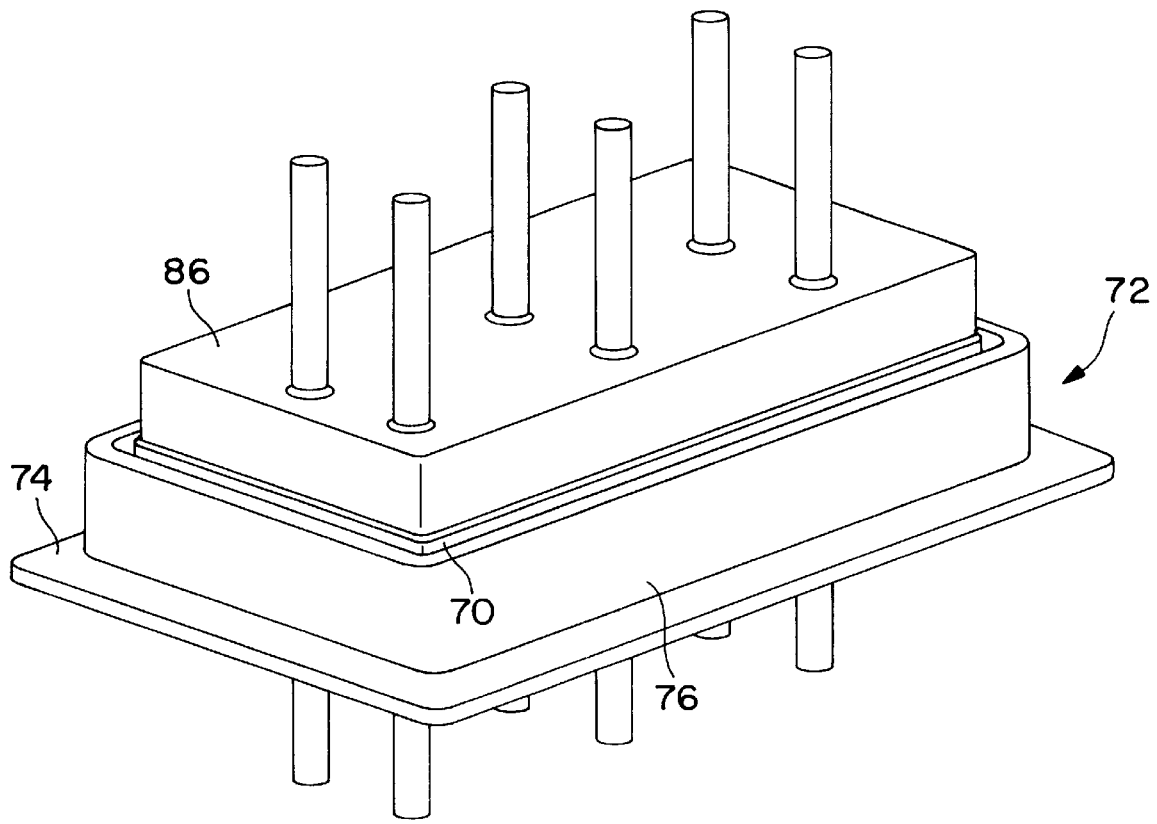
FIG. 8 is a perspective view similar to FIG. 6 illustrating a capacitor array located on top of the varistor array.

In FIG. 8, a capacitor array device 86 is situated on top of varistor array 70. As described above with reference to other embodiments, capacitor array 86 functions to provide desired secondary filtering at lower frequencies. One skilled in the art will appreciate that various suitable techniques may be employed to electrically connect the common terminal of capacitor array 86 to header 72.

Figure 9:
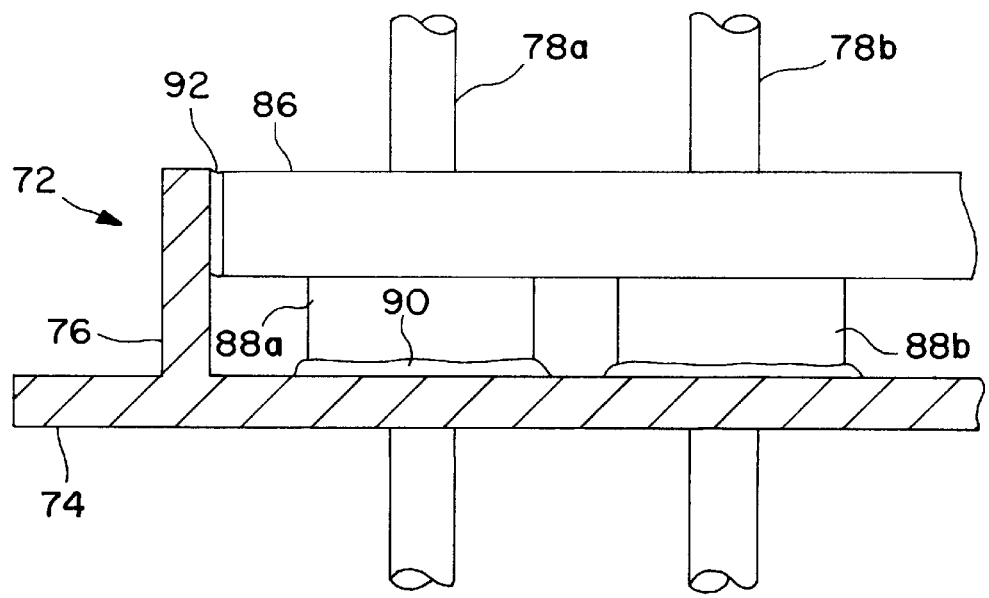
FIG. 9 is a partial cross-sectional view illustrating a further embodiment wherein individual discoidal varistors are situated about the respective terminal leads with a capacitor array located on top.

FIG. 9 illustrates a further alternative wherein individual varistors are associated with each of the terminal leads. For example, in the illustrated embodiment, discoidal varistors 88a–b are positioned about respective terminal leads 78a–b. A bead 90 of solder, conductive epoxy or other suitable conductive means is placed at the base of the respective discoidal varistors to provide electrical connection with header 72.

As shown, capacitor array 86 may be located on top of the individual discoidal varistors to provide desired secondary filtering. In many embodiments, capacitor array 86 may fit within the confines of peripheral wall 76. The common terminal of array device 86 is electrically connected to peripheral wall 76 at 92.

It can be seen that the present invention discloses various novel filtering arrangements such as may be utilized in an implantable medical device. As a particular advantage, the invention may permit the use of smaller filtering capacitors than have been used in the past. For example, capacitors having a relatively high voltage rating may have been required in order to prevent damage caused by a voltage transient. The transient suppression characteristics of the present invention limit the voltage levels transmitted into the implantable device.

While various constructions are contemplated by the present invention, one skilled in the art will appreciate that variations and modifications may be made without departing from the invention. It should also be understood that aspects of the various embodiments may also be interchanged both in whole or in part. Furthermore, those of ordinary skill in the art will appreciate that the foregoing description is by way of example only, and is not intended to be limitative of the invention so further described in such appended claims.

What is claimed is:

1. A feed-through filter comprising:
    a conductive mounting element;
    at least one elongate terminal member maintained in electrically insulated relation with respect to said conductive mounting element;
    a varistor structure supported by said conductive mounting element and defining a respective feedthrough hole through which said elongate terminal member extends, said varistor structure having a plurality of first polarity plates interleaved with a plurality of second polarity plates; and
    said first polarity plates being electrically connected to said elongate terminal member and said second polarity plates being electrically connected to said conductive mounting element.

2. A feed-through filter as set forth in claim 1, wherein said varistor structure has a discoidal configuration.

3. A feed-through filter as set forth in claim 2, further comprising a discoidal capacitor structure mounted axially adjacent to said varistor structure along said elongate terminal member.

4. A feed-through filter as set forth in claim 2, wherein said conductive mounting element comprises a conductive canister in which said varistor structure is maintained.

5. A feed-through filter as set forth in claim 4, comprising at least two of said elongate terminal members extending through said varistor structure.

6. A feed-through filter as set forth in claim 2, wherein said conductive mounting element comprises a conductive mounting plate.

7. A feed-through filter as set forth in claim 6, wherein said conductive mounting plate defines a wall element around a periphery thereof.

8. A feed-through filter as set forth in claim 1, comprising a hermetic seal arrangement to maintain said at least one elongate terminal member in electrically insulated relation with respect to said conductive mounting element.

9. A feed-through filter as set forth in claim 1, wherein said varistor structure comprises a multilayer metal-oxide varistor.

10. A feed-through filter as set forth in claim 9, wherein said multilayer metal-oxide varistor comprises a zinc-oxide varistor.

11. A feed-through filter comprising:
a conductive canister;
at least one elongate terminal member maintained in electrically insulated and hermetically sealed relation with respect to said conductive canister;
a discoidal varistor structure supported by said conductive mounting element and defining a respective feedthrough hole through which said elongate terminal member extends, said varistor structure having at least one first polarity plate situated in respective opposition to at least one second polarity plate; and
said first polarity plate being electrically connected to said elongate terminal member and said second polarity plate being electrically connected to said conductive canister.

12. A feed-through filter as set forth in claim 11, wherein said varistor structure comprises a metal-oxide varistor.

13. A feed-through filter as set forth in claim 12, wherein said metal-oxide varistor comprises a multilayer zinc-oxide varistor.

14. A feed-through filter as set forth in claim 11, further comprising a discoidal capacitor structure mounted axially adjacent to said discoidal varistor structure.

15. A feed-through filter as set forth in claim 11, comprising at least two of said elongate terminal members extending through said varistor structure.

16. A filtering arrangement for use in an implantable medical device, said arrangement comprising:
a conductive mounting element adapted to be connected to an outer shell of said implantable medical device in hermetically sealed relation therewith;
at least one elongate terminal member maintained in electrically insulated and hermetically sealed relation with respect to said conductive mounting element;
a first filter structure supported by said conductive mounting element and operative to provide transient suppression and to filter interference signals carried by said elongate terminal member above another predetermined threshold frequency;
said first filter structure having a first polarity terminal electrically connected to said elongate terminal member and a second polarity terminal electrically connected to said conductive mounting element; and
a second filter structure having a first polarity terminal electrically connected to said elongate terminal member, said second filter structure operative to filter interference signals carried by said elongate terminal member below said predetermined threshold frequency.

17. A filtering arrangement as set forth in claim 16, wherein said first filter structure comprises a multilayer varistor structure defining a varistor feedthrough hole through which said elongate terminal member extends.

18. A filtering arrangement as set forth in claim 17, wherein said multilayer varistor structure comprises a discoidal varistor structure.

19. A filtering arrangement as set forth in claim 17, wherein said multilayer varistor structure comprises a multilayer metal-oxide varistor.

20. A filtering arrangement as set forth in claim 17, wherein said second filter structure comprises a multilayer capacitor structure having a capacitor feedthrough hole through which said elongate terminal member extends.

21. A filtering arrangement as set forth in claim 20, wherein said multilayer capacitor structure is mounted axially adjacent to said multilayer varistor structure.

22. A filtering arrangement as set forth in claim 21, wherein said multilayer capacitor structure is mounted axially separated from said multilayer varistor structure.

23. A filtering arrangement as set forth in claim 17, wherein said second filter structure comprises a surface mount capacitor electrically connected to said elongate terminal member.

24. A filtering arrangement as set forth in claim 16, wherein said conductive mounting element comprises a conductive canister in which at least said first filter structure is maintained.

25. A filtering arrangement as set forth in claim 24, wherein said first filter structure comprises a multilayer varistor structure having a discoidal configuration.

26. A filtering arrangement as set forth in claim 16, wherein said conductive mounting element comprises a conductive mounting plate.

27. A filtering arrangement as set forth in claim 26, wherein said conductive mounting plate defines a wall element around a periphery thereof.

28. A feed-through filter comprising:
a conductive mounting plate;
a plurality of elongate terminal members maintained in electrically insulated relation with respect to said conductive mounting plate;
a varistor array structure supported by said conductive mounting plate and defining a plurality of feedthrough holes through which said elongate terminal members respectively extend;
said varistor array structure including a plurality of varistor devices each associated with a respective one of said elongate terminal members, each of said varistor devices having at least one first polarity plate electrically connected to said one of said elongate terminal members, each of said varistor devices further comprising at least one second polarity plate electrically connected to said conductive mounting plate.

29. A feed-through filter as set forth in claim 28, wherein said at least one second polarity plate for each of said varistor devices comprising a common plate for all of said varistor devices.

30. A feed-through filter as set forth in claim 28, wherein said conductive mounting plate defines a wall element around a periphery thereof.

* * * * *